United States Patent
Robbat, Jr.

(10) Patent No.: US 6,487,920 B1
(45) Date of Patent: *Dec. 3, 2002

(54) SITU SOIL SAMPLING PROBE SYSTEM WITH HEATED TRANSFER LINE

(75) Inventor: Albert Robbat, Jr., Andover, MA (US)

(73) Assignee: Trustees of Tufts College, Medford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 912 days.

(21) Appl. No.: 08/791,520

(22) Filed: Jan. 30, 1997

(51) Int. Cl.[7] .................................................. G01N 1/00
(52) U.S. Cl. ................................. 73/863.12; 73/864.74
(58) Field of Search .......................... 73/863.11, 863.12, 73/864.34, 864.73, 864.74, 864.81; 175/20, 21, 40, 50, 58, 59, 60; 166/264; 374/148

(56) References Cited

U.S. PATENT DOCUMENTS

| | | | |
|---|---|---|---|
| 2,386,832 A | * 10/1945 | Zaikowsky et al. | 73/864.73 |
| 4,735,259 A | 4/1988 | Vincent | 165/47 |
| 4,985,625 A | 1/1991 | Hurst | 25/288 |
| 4,989,678 A | 2/1991 | Thompson | 175/20 |
| 5,010,776 A | 4/1991 | Lucero et al. | 73/863.23 |
| 5,072,981 A | 12/1991 | Weaver et al. | 294/102.1 |
| 5,098,451 A | 3/1992 | Roundehler et al. | 55/67 |
| 5,119,290 A | 6/1992 | Loo et al. | 395/400 |
| 5,123,274 A | 6/1992 | Carroll et al. | 73/1 G |
| 5,127,343 A | 7/1992 | O'Ham | 110/233 |
| 5,272,089 A | 12/1993 | Vo-Dinh | 436/126 |
| 5,272,337 A | 12/1993 | Thompson et al. | 250/288 |
| 5,358,057 A | 10/1994 | Peters et al. | 175/20 |
| 5,395,589 A | 3/1995 | Nacson | 422/88 |
| 5,402,668 A | 4/1995 | Murakami et al. | 73/19.2 |
| 5,415,025 A | 5/1995 | Bartman et al. | |
| 5,587,538 A | * 12/1996 | Bratton | 73/864.74 |

OTHER PUBLICATIONS

"Silcosteel," *Alltech Associates, Inc., Deerfield, IL*, Technical Brochure (Jan. 1994).

McDonald, et al., "Developments and Applications of Field Mass Spectrometers," *Environ. Sc. Technol.*23(7) :336–343 (1994).

"Short Path Thermal Desorption Model TD–3," SIS Thermal Desorption, (http://www.sisweb.com/sptd/sdpt-main.htm), pp. 1–2, 1–5, 1–2 (no date given).

(List continued on next page.)

*Primary Examiner*—Robert Raevis
(74) *Attorney, Agent, or Firm*—Hamilton, Brook, Smith & Reynolds, P.C.

(57) ABSTRACT

The present invention is directed both to an improved in situ penetrometer probe and to a heated, flexible transfer line. The line and probe may be implemented together in a penetrometer system in which the transfer line is used to connect the probe to a collector/analyzer at the surface. The probe comprises a heater that controls a temperature of a geologic medium surrounding the probe. At least one carrier gas port and vapor collection port are located on an external side wall of the probe. The carrier gas port provides a carrier gas into the geologic medium, and the collection port captures vapors from the geologic medium for analysis. In the transfer line, a flexible collection line that conveys a collected fluid, i.e., vapor, sample to a collector/analyzer. A flexible carrier gas line conveys a carrier gas to facilitate the collection of the sample. A system heating the collection line is also provided. Preferably the collection line is electrically conductive so that an electrical power source can generate a current through it so that the internal resistance generates heat.

32 Claims, 8 Drawing Sheets

OTHER PUBLICATIONS

K.F. Meyers, et al., "Laboratory Evaluation of a Volatile Organic Compound Analysis System for the Site Characterization and Analysis Penetrometer System," pp. 176–184 (no date given).

J.H. Ballard, et al., "Site Characterization and Analysis Penetrometer System (SCAPS), " *U.S. Army Engineer Waterways Experiment Station, 3909 Halls Ferry Road, Vicksburg, Mississippi 39180–6199* (no date given).

T. Rymen, et al., "Home–Made Thermal Desorption Unit as an Aid in Gas Chromatographic/Mass Spectrometric Identification of Environmental Pollutants," *Analytica Chimica Acta*, 196, pp. 85–93 (1987).

"The MM–1 Mobile Mass Spectrometer User Manual," Bruker–Franzen Analytik GmbH, pp: 0–1—12–19 (Feb. 1987).

E.B. Overton, et al., "Field Deployable Instrument for the Analysis of Semivolatile Organic Compounds," *60–Waste Treatment*, vol. 114, pp. 411 (1991).

E.B. Overton, et al., "Field Deployable Instrument for the Analysis for Semivolatile Organic Compounds," *80–Organic Anal. Chem.*, vol. 114 (1991).

W.L. Bratton et al., "Direct Penetration Technology for Geotechnical and Environmental Site Characterization," *Geoenvironment*, vol. 1 , pp. 105–123 (1995).

S. Piccoli, et al., "Geo–Environmental Testing Using the Envirocone," *Geoenvironment*, vol. 1, pp. 93–103 (1995).

C.Y. Chiang, "Field Determination of Geological/Chemical Properties of an Aquifer by Cone Penetrometry and Headspace Analysis," *Ground Water*, 30(3):428–436 (May–Jun. 1992).

K.F. Meyers, "Laboratory Evaluation of a Volatile Organic Compound Analysis System for the Site Characterization and Analysis Penetrometer System," *US Army Corps of Engineers*, Technical Report IRRP–95–3 (Sep. 1995).

Morvai, M., et al., "Simultaneous Gas–Liquid Chromatographic Determination of Sugars and Organic Acids as Trimethylsilyl Derivatives in Vegetables and Strawberries," *Journal of Chromatography*, 552, pp. 337–344 (1991).

* cited by examiner

SITU SOIL SAMPLING PROBE SYSTEM WITH HEATED TRANSFER LINE

GOVERNMENT SUPPORT

This invention was made with government support under Contract No. ANL-941922402 awarded by the Department of Energy. The Government has certain rights in this invention.

BACKGROUND OF THE INVENTION

In recent years, public attention has been directed to subsurface soil/groundwater contamination by toxic wastes. Increased governmental and private resources have been devoted to both assessing the extent/concentration of the contaminants and also remediation.

The most commonly used technique for detecting subsurface contaminants is soil sampling. A bore hole is drilled to a desired depth, with a sample of the soil being physically collected. The sample is cataloged and sent to a laboratory to determine the type and concentrations of contaminants contained in the soil typically using solvent extraction techniques. This approach, while providing the accuracy and precision of laboratory analysis, is both slow and costly. Separate bore holes are usually drilled for each sample collected, and the transportation of the sample to the laboratory followed by analysis require days to weeks before the results are available.

Cone penetrometer technology has been developed as a solution to some of the problems associated with physical collection/laboratory analysis. Typically, a cone penetrometer is advanced or pushed through the soil by lengths of drilling rod or pipe that connect the probe to a hydraulic pushing device, typically located in a truck. The penetrometer can be configured to collect multiple samples as it is advanced through the soil or, in some situations, tests the soil samples in situ. According to one technology, the end of the penetrometer probe is opened, and then the probe is advanced slightly to collect a small sample of soil in a chamber within the probe. Gases are collected from the soil as it is moderately heated, and the gases carried through collection tubes to the surface. There, gas chromotomography can be performed to identify contaminants in the soil.

Existing in situ cone penetrometer technology finds only limited practical use due to its poor accuracy/precision. The efficiency with which the soil contaminants may be identified is relatively poor compared to laboratory soil analysis. For example, the effective sample size of the previously-mentioned probe is limited by the size of its chamber, which in turn is only some fraction of the probe's overall width. Small sample sizes lead to low detection limits. Moreover, the existing technology generally provides a high level of inter-sample contamination. That is, the contaminants collected from earlier samples tend to accumulate in the probe, distorting the results of later sampling events.

SUMMARY OF THE INVENTION

The present invention is directed both to an improved in situ penetrometer probe and to a heated, flexible transfer line. In the preferred embodiment, they are implemented together in a penetrometer system in which the transfer line is used to connect the probe to the surface.

In general, the inventive probe comprises a heater that controls a temperature of a geologic medium surrounding the probe. At least one carrier gas port and vapor collection port are located on an side wall of the probe. The carrier gas port provides a carrier gas into the geologic medium, and the collection port captures vapors from the geologic medium for analysis.

The heating of the surrounding soil enables both the debinding of chemicals otherwise locked in the soil and the collection without the need to draw the soil into the probe as in some prior art designs. The location of the ports on the side wall of the probe offers a number of further advantages over the prior art configurations. First, the construction need not be overly complex. Carrier gas and collection lines can be terminated in the side wall without requiring moving parts. More importantly, however, is the fact that soil is not drawn into the probe. Thus, there are no contaminants trapped in the probe to undermine the accuracy of subsequent samples. Soil from earlier samples is stripped from the probe's exterior as it is advanced for the next sampling. Thus, the inventive probe does not suffer from measurement accuracy or precision problems, when vapor samples are gathered at different depths.

In embodiments, at least one, but preferably two or more vapor collection ports are spaced around a circumference of the probe. Corresponding carrier gas ports are also circumferentially located around the probe. Alternatively, in other embodiments, multiple collection and carrier gas ports can be spaced axially along the probe.

In the preferred embodiment, the probe comprises a temperature transducer to detect the temperature of the geologic medium surrounding the probe. The heater is capable of raising the temperature of this medium to greater than 200° C., and preferably to approximately 400° C. or greater. These temperatures are substantially higher than those obtained in many prior art devices, which worked in the approximately 100° C. temperature range. This shortcoming was one reason why the prior art failed to achieve accurate results. Research associated with the present invention has shown that the higher temperatures are required to debind many types of contaminants, especially semi-volatile organic compounds, from the soil.

In still other embodiments, the carrier gas, which is injected into the surrounding soil, may be heated. In this way the soil can be directly heated with hot gas thereby reducing or eliminating the need for the heater in the probe.

In general, the invention also relates to a method for thermally extracting subsurface chemicals from soil with a high water content. This method comprises first advancing a probe through the soil to a desired depth. The soil surrounding the probe is then heated to at least 100° C., preferably 120° C., while a carrier or similar gas is exhausted into the soil. This has the effect of pushing water vapor away from the probe's collection port. After this is completed, the soil is heated to substantially higher than 100° C., and vapor is collected from the soil. Since the moisture content of the surrounding soil has been substantially reduced, more contaminates are found in the collected vapor since high moisture tends to keep the contaminants in the soil.

In the preferred embodiment, before future sampling, any contaminants remaining in the collection line are preferably backflushed back out of the line.

In general, according to another aspect, the invention also features the heated transfer line system. In the system, at least one flexible collection line conveys a collected fluid, i.e., vapor sample. At least one flexible carrier gas line conveys a carrier gas to facilitate the collection of the sample. The collection line is also heated.

The flexibility of the line is required by the penetrometer system because the line must pass through the pipe sections when they are stacked, i.e., not connected. Specifically, the line should have a bending radius of approximately 10 inches or less. In the preferred embodiment, the bending radius is 4 inches or less.

The flexibility of the line also enables its use in other applications and thus the line is not limited to penetrometer systems. For example, in smoke-stack emissions or airport bomb detection, a flexible transfer line is useful to carry a vapor sample from some remote location to a collector/analyzer.

When implemented in a penetrometer system, the line must be relatively long, greater than 50 feet and as long as 300 feet. These lengths are required because the line must pass through the pipe section in the soil but also the disconnected sections stacked in the truck.

A number of different options may be used to heat the collection line. Heating filaments or other heating device may be laid with the line. In the preferred embodiment, however, the collection line is electrically conductive so that an electrical power source can generate a current through it. Therefore, the collection line's internal resistance heats the line. In either case, the heating capability should be strong enough to raise the line's temperature to at least 280° C. to keep contaminants, particularly semi-volatile organic compounds, vaporized in the line and later remove any condensed water during backflushing. In the preferred embodiment, the line may be heated to 200–400° C. These temperatures are needed to debind many chemicals from the line's walls if adsorbed to ensure that subsequent samples are not tainted.

The high temperatures at which the collection line may be maintained distinguish the invention from penetrometer systems in the prior art. While prior art probes had capabilities to heat the soil, any semi-volatile organic compounds that were vaporized could not be carried to the surface. They condensed in the cooler transfer line. In contrast, the present line can be uniformly heated so that the compounds remain vaporized, allowing the carrier gas to transport them to the surface.

In the preferred embodiment, the collection line is surrounded by at least one thermally insulating layer. At least one electrically insulating layer is also used. A slippery layer promotes flexibility allowing layers to slip with respect to each other. The insulating layers are needed so that the collection line's temperature may be uniformly maintained across it extended 100 foot or more length. A somewhat related requirement is the fact that the temperatures and electric fields generated around the line must not endanger the personnel operating the line even in wet environments. Thus, various layers must also keep the line's surface temperatures low enough to avoid burns and seal the line to prevent shock.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
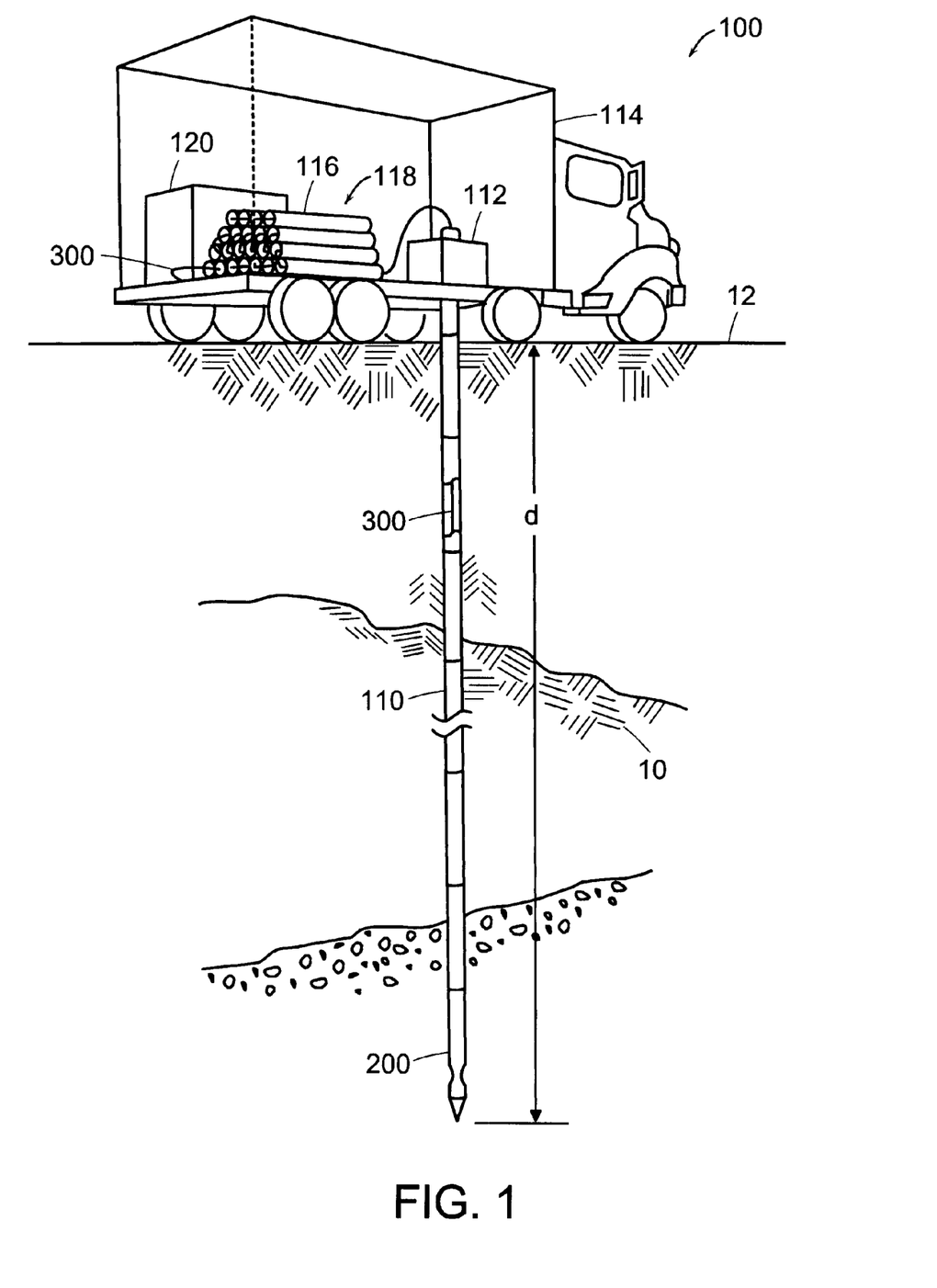
FIG. 1 is a perspective schematic, partially cut-away view showing the inventive penetrometer system.

FIG. 1 is a schematic perspective drawing of a penetrometer system using an in situ thermal extraction penetrometer probe 200 with heated transfer line 300, which have been constructed according to the principles of the present invention.

Generally, the penetrometer system 100 comprises a usually conically-tipped sampling probe 200 that is advanced substantially vertically through a geologic medium 10, i.e., soil, by connected sections of drill rod or pipe 110. An hydraulic pushing device 112, typically housed in a truck 114 at the surface 12, grasps the top end of the connected sections of drill rod 110 to physically advance the 200 deeper into the soil, or subsequently, withdraw the drill rod sections, when the sampling has been completed. New pipe sections 116 are removed from a stack 118 in the truck 114 and attached to the connected sections by complementary threads between the new section and the section that was last attached.

The hydraulic pushing device 112 typically applies tens of tons, approximately forty tons in newer designs, of downwardly-directed force to the drill rod sections 110. As the drill rod 110 is advanced, the truck 114, in many cases, is lifted from the ground, only to slowly settle as the drill rod slowly advances forward. Although largely dependent upon the characteristics of the geologic medium and the diameter of the drill rod sections, depths on the order of d=100–200 feet or greater can be achieved under favorable conditions. The invention, however, is relevant at depths of a few inches, where adequate head pressure may be developed, to whatever depth is achievable by pushing or otherwise placing the probe.

The inventive penetrometer probe 200 provides for in situ subsurface sampling of gas, or fluids generally, from the geologic medium 10 surrounding the probe 200. The heated transfer line 300, which is threaded both through the connected sections of pipe 110 and those new sections 116 in the stack 118 in the truck, conveys fluid samples from the probe 200 up to the truck. There the samples are collected and possibly analyzed in collector/analyzer 120, making in-the-field analysis possible.

Figure 2A:
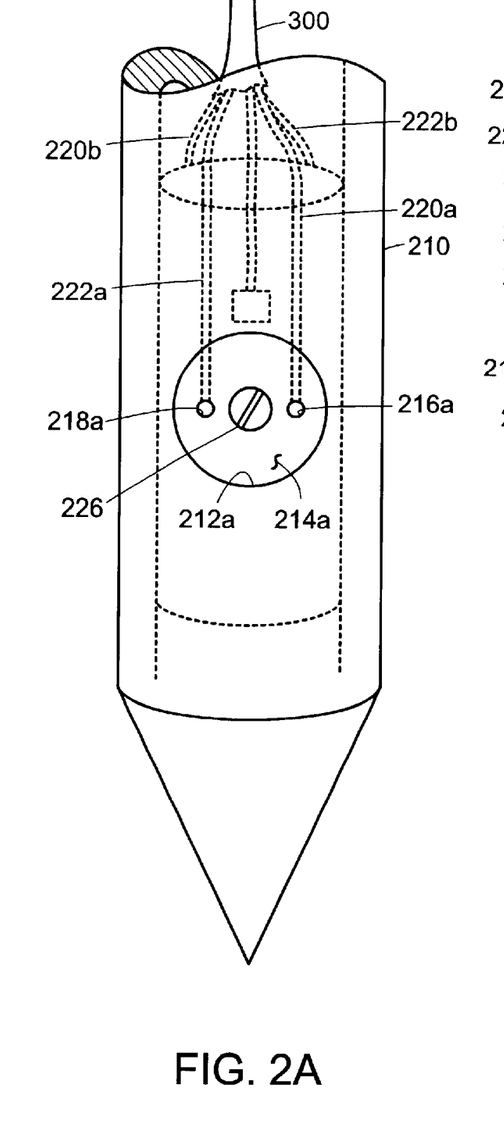
FIG. 2A is a side view of the inventive probe.

FIG. 2A is a side view of the inventive probe 200. The outer surface of the probe is substantially defined by a section of drill rod or pipe 210 used for the probe. Two, preferably round, circumferentially opposed holes 212A,B are machined in the pipe 210 to accommodate two opposed port plugs 214A,B. See also FIG. 2B. A carrier gas port 216A and a vapor/fluid collection port 218A are provided in the plug 214A so that a carrier gas may be exhausted or provided into soil surrounding the probe 200 and vapor or fluid then collected from the soil. Another pair of ports 216B, 218B, not shown, are located in the other plug 214B. The ports 216A, 218A are in fluid communication with a respective carrier gas line 220A and a collection line 222A, shown in phantom. Similar lines 220B, 222B support ports 216B, 218B in plug 214B. All four lines are physically collected together in the heated transfer line 300 that passes to the surface 12 through the drill rod sections 110.

In other implementations, port plugs are not necessarily used. The carrier gas and vapor/fluid collection ports 216, 218 may be formed directly through the side wall of the pipe section 210. The use of the plugs, however, facilitates the connection of the carrier gas lines 220 and collection lines 222.

Other implementations use more or less than two pairs of ports 216, 218. For example, additional sets of ports are alternatively stacked, one above the other, along the pipe's length. Further, one or three or more sets of ports 216, 218 can be placed around the pipe's circumference.

Figure 2B:
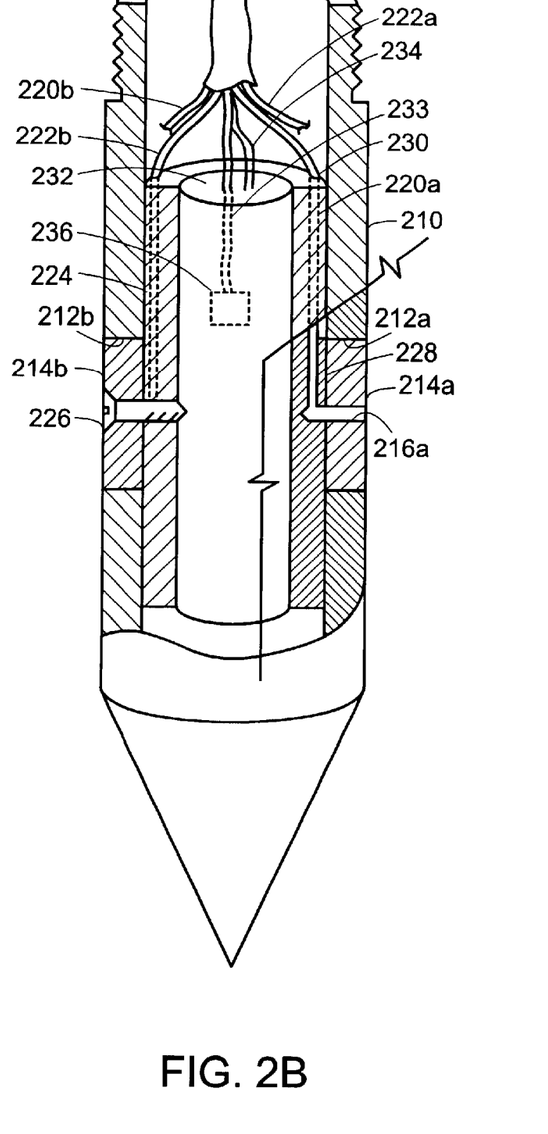
FIG. 2B is a partial cutaway view of the inventive probe.

FIG. 2B is a partial cutaway view showing the internal construction of the probe 200. Each of the port plugs 214A,B is secured, by respective bolts 226, to a metal sleeve 224 in the interior, hollow core of the pipe 210. The horizontally extending ports 216, 218 in the port plugs 214 are in communication with substantially vertical bores 228 in the sleeve 224. The carrier gas and collection lines 220, 222 terminate in the separate, respective bores 228 and are sealed to them. These lines 220, 222 are laid in channels 230 formed in the sleeve 224 as they ascend vertically to the transfer line 300.

A heater cartridge 232 is housed within the sleeve 224 and is electrically connected to the surface via electrical lines 234 that are also contained in the transfer line 300. A temperature sensor 236, thermocouple, is also located in the probe 200 to enable temperature detection and facilitate feed-back control of the heater cartridge 232. Electrical lines 233 carry the sensor's signals to the surface.

Alternatively, the soil surrounding the probe 100 can be heated by heating the carrier gas that is injected into the soil. This technique can obviate the need for the heater cartridge 232. Some mechanism, however, is required to heat the carrier gas on the way to the probe or in the probe 100. Heating in the truck is generally inadequate since the gas will be cool by the time it reaches the probe. The carrier gas can be easily heated by laying the carrier gas line with the heated collection line described below.

Soil testing sensors may be additionally added to the probe 300. Example, electrodes may be located on the probes exterior to perform soil electrical conductivity measurements. Additionally, a pH sensor may be located in the probe to detect soil pH.

Figure 3:
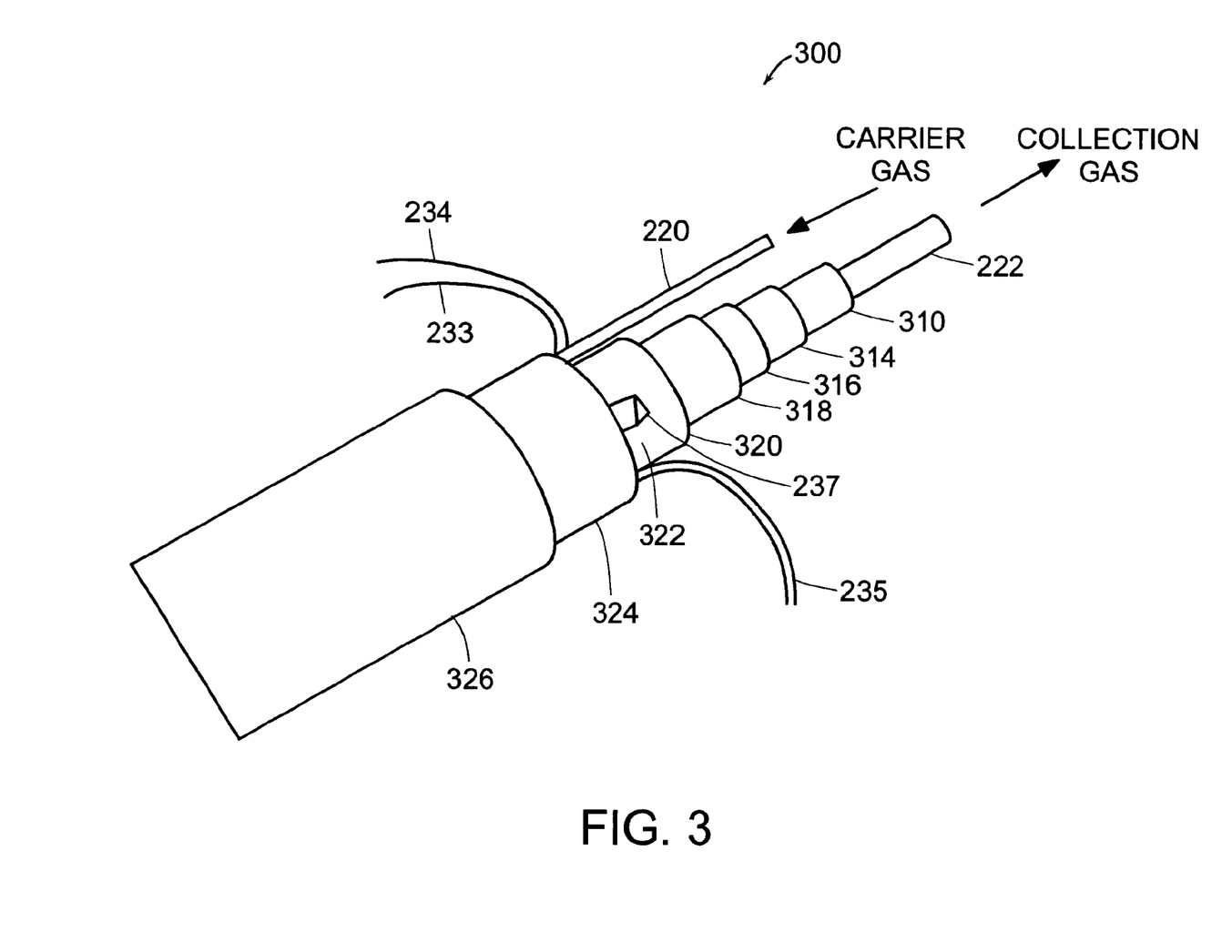
FIG. 3 is a perspective view showing the construction of the inventive transfer line.

FIG. 3 shows the construction of the heated transfer line 300 of the present invention. Generally, it contains, at its center, the one or more collection lines 222 running from the collection ports 218 of the probe 200. A number of separate, surrounding layers both electrically and thermally insulate the collection line 222. Interspersed layers promote the line's flexibility, allowing layers to slide relative to each other. The carrier gas line 220 is laid near the outer periphery along with the electrical cables 233,234 to the probe's cartridge heater 232 and temperature sensor 236. Additional electrical wiring 235 is provided for possibly one or more additional temperature sensors 237 along the length of the heated transfer line 300. Finally, outer layers bind the electrical cables 233, 234, 235 and carrier gas line 220 to the package along with providing resistance to abrasive wear.

The thus constructed heated transfer line 300 has a comparatively high degree of flexibility. The surrounding insulation and flexibility-promoting layers allow the heated transfer line to have a bending radius less than 10", preferably as small as 4" or even 2 to 3". These bending radii are not necessary in the connected sections 110 of the drill rod since here the line is relatively straight. In the truck 114, however, the transfer line 300 must thread through the sections 116 on the stack 118, necessitating the need for the flexibility. Otherwise the rod sections can not be stacked near enough to each other to be accommodated within the truck.

In more detail, both the collection line 222 and the carrier gas line 220 are preferably constructed from metal tubing. Such tubing will not collapse when negative pressures are applied to draw gases from the soil or burst with high positive pressures needed to force carrier gas into the soil. The metal is also relatively unaffected by high temperatures. It is especially important, however, that at least the collection line 222 is relatively inert with respect to the fluids it transports. The collection line should neither react with any of the fluids nor catalyze reactions in the fluids. Deactivated, fused silica lined stainless steel tubing is used in the preferred embodiment. Such tubing is commercially available under the brand name SILCOSTEEL®. Because the heated transfer line must be flexible, the outside diameter of the collection and carrier gas lines must be relatively small. Tubing with an 1/8" outside diameter (OD) has a minimum bending radius of approximately 3" without crimping, which is acceptable here.

In the preferred embodiment, a separate heating element is not placed in proximity to the collection line 222 to control its temperature. Instead, electrical current is directed through the line 222 itself. A controlled voltage source is connected to the proximal end of the line in the truck, with the line end in the probe being at a ground potential. The inherent resistance of the stainless steel line serves to generate the heat necessary to control its temperature.

In some embodiments, however, it may be preferable to use a separate heating element to maintain the temperature of the collection line 222 such as wrapped NiChrome wire. Experiments involving the use of a separate, wrapped heating element, however, have resulted in uneven heating of the collection line unless a tight wrapping pattern is used, which increases the transfer line's material cost and weight, while reducing its flexibility. Thus, at present, these embodiments are not preferred.

The collection line 222 is preferably surrounded by a first insulation layer 310. The insulation should have good high temperature characteristics. High temperature sleeving under the brand name NEXTEL 312 is preferred.

The first insulation layer is preferably surrounded by a flexible and slippery layer 314 to allow some inter-layer movement. TEFLON® tubing is used in the preferred embodiment. An aluminum foil layer 316 is wrapped around the TEFLON® sleeve layer 314, and a polyamide insulation layer 318 is applied to the aluminum foil. Type 5413 polyamide film tape by the 3M® Company is preferred. A fiberglass cloth insulation 320 is applied over the polyamide insulation. This provides good thermal and electrical insulation. SCOTCH® 69 glass cloth electrical tape is preferably used.

The carrier gas tube 220 and the electrical cables 233–235 are then laid over the fiberglass insulation layer 320 extending axially along the heated transfer line's length. The carrier gas line 220 can be similarly constructed from deactivated, fused silica stainless steel tubing with an 1/8" OD. The non-reactive characteristics here, however, are less important since this line, in most situations, merely conveys the non-reactive carrier gas.

Silicone adhesive pressure sensitive tape 322 or similar product is used to bind the electrical cable 233, 234, 235 and carrier gas tube 220 to the heated transfer line core. Fiberglass cloth tape 324 provides an added layer of electrical and thermal insulation around the silicone tape 322. The outer bundle is finally covered by flexible polyolefin heat shrink sleeve 326. One inch expanded diameter tube can be used. The tube is purchased under the brand name COMCO. This last layer provides good resistance to abrasive wear between transfer line 300 and the inner bore of the drill rod or pipe sections 110.

The various layers of the heated transfer line 300 provide adequate insulation to the collection line 222 so that heat loss to the environment along its length can be balanced by the heating capacity of the electrified line. The thermal insulating properties of the layers additionally maintain the line's surface temperatures low enough to allow operator manipulation of the line without the risk of temperature burns. Moreover, the layers also seal-out moisture to prevent the risk of shock.

Figure 4:
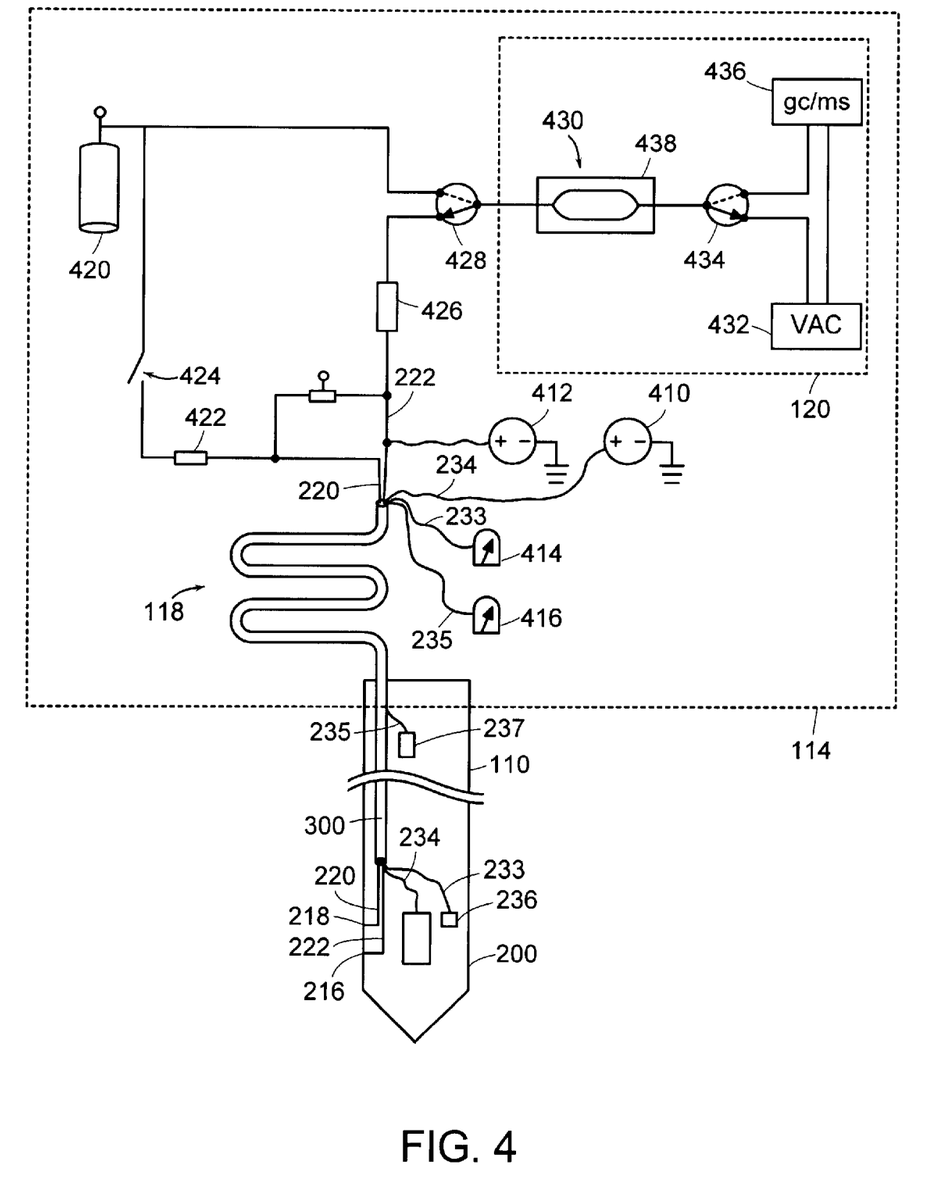
FIG. 4 is a schematic electrical and fluid circuit diagram for the penetrometer system of the present invention.

FIG. 4 is a schematic electrical and fluid circuit diagram for the penetrometer system 100 of the present invention that supports the in situ sampling and field analysis. The collection line 222 and carrier gas line 220 pass up through the heated transfer line 300 from the probe 200 in the connected sections of drill rod 110 to the portion of the heated transfer line contained in the drill rod stack 118 in the truck 114. The electrical cables 233–235 also pass through these portions. In the truck, on the proximal side of the stack 118, the several electrical cables are separated. Cables 234 to the cartridge heating element 232 are connected to a controlled voltage source 410. The collection line 222 itself is electrically connected to a second controlled voltage source 412. Finally, the electrical lines 233, 235 to the temperature sensors, both in the probe (236) and along the length of the collection line (237), are connected to displays 414, 416 and possibly for automatic feedback control of the cartridge heater voltage source 410 and the source 412 that passes current through the collection line 222.

In the truck, the carrier gas line 220 is connected to a gas source 420 through a filter 422 and an on/off valve 424. The carrier gas source 420 typically supplies either helium or nitrogen.

The collection line 222 is connected through a flow meter 426 and switching valve 428 to an inlet port of a thermal deadsorber/adsorber unit 430. This is a dry ice-cooled glass-lined sleeve that traps and concentrates hot organic vapor in the collected gas samples. The flow meter 426 measures the gas volume passing through the line, and the inlet switching valve 428 alternatively connects the inlet port to the collection line 222 or the carrier gas source 420. A second switching valve 434 on the outlet side of the thermal adsorber/desorber 430 connects it to either a vacuum unit 432 or a gas chromotomographer/mass spectrometer (GC/MS) unit 436. When gas sample collection occurs, the inlet switching valve 428 connects the adsorber unit 430 to the collection line 222, and the outlet switching valve 434 connects it to the vacuum 432.

Once a sample has been collected in the adsorber unit 430, the inlet valve 428 is switched to the carrier gas supply 420 and the outlet valve 434 is switched to the GC/MS 436. The adsorber unit's operation is switched to that of a thermal desorber. The dry ice is removed and the unit ballistically heated by the surrounding heater block 438. Carrier gas flushes the now-concentrated sample into the GC/MS 436.

Details regarding the use of the GC/MS and gas analysis techniques preferably used with the present invention are described in the U.S. patent application Ser. No. 08/639,183, filed on Apr. 26, 1996, entitled "Methods and Apparatus for Analysis of Complex Mixtures", by Albert Robbat, Jr. and Yuriy V. Gankin, the teachings of which are incorporated herein in their entirety by this reference.

Alternative embodiments use other analysis devices for organics. Examples include: gas chromotography/flame ionization detector (GC/FID), gas chromotography/electron capture detector (GC/ECD), and infrared (IR) spectrometer type devices.

Figure 5:
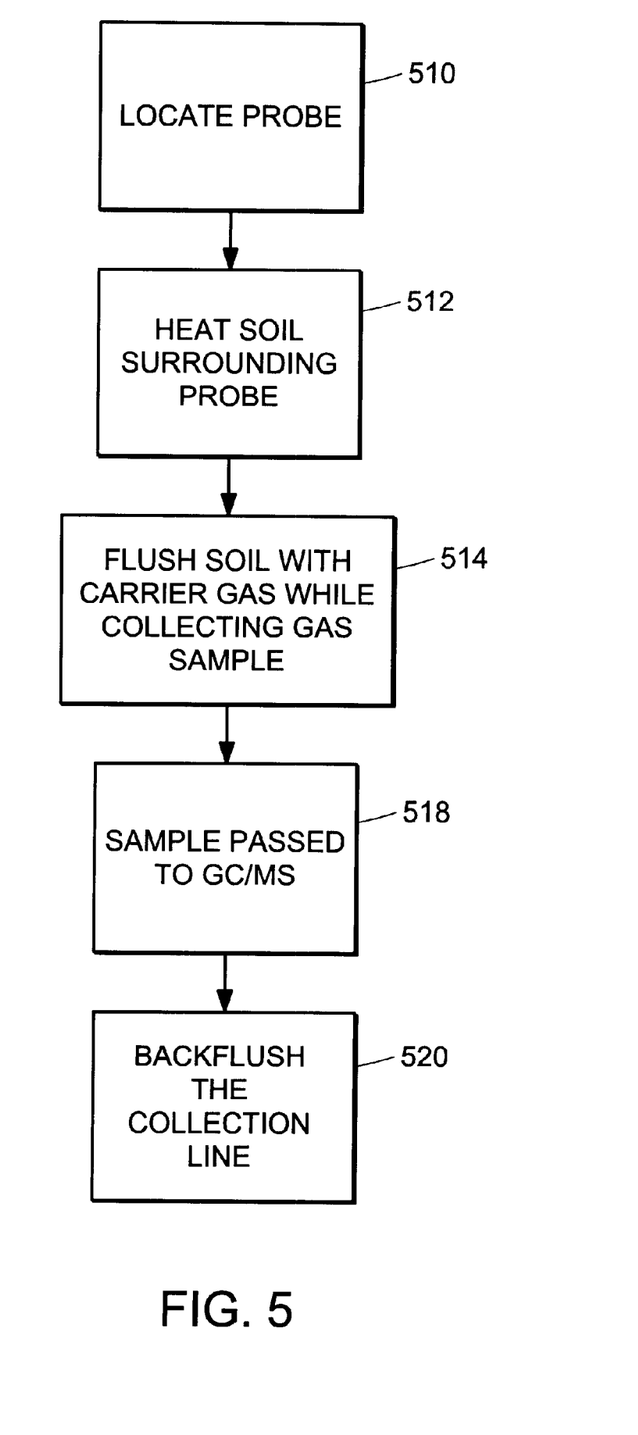
FIG. 5 is a process diagram illustrating the use of inventive penetrometer system.

FIG. 5 is a process diagram illustrating the use of inventive penetrometer system 100. The probe 200 is advanced by the pushing device 112 to the desired depth in step 510. The soil surrounding the probe 200 is then heated to the temperature necessary to extract the chemicals of interest from it in step 512. The heater cartridge 232 in the probe 200 is powerful enough to raise the temperature of the surrounding soil to as high as 400° C. or greater. These temperatures are necessary to free contaminants chemically bound to the soil such as semi-volatile organic compounds.

The carrier gas is used to move the chemicals from the surrounding heated soil to the collector/analyzer 120. At least twenty dead volumes of carrier gas are injected into the soil surrounding the probe 200 through the carrier gas ports 216 in step 514. Simultaneously, the collected gas is drawn up to through collection ports 218 into the collection line 222 into the adsorber unit 430 by the vacuum 432. The cold temperature of the adsorber unit condenses and traps chemicals in the carrier gas. The adsorber/thermal desorber is then isolated, its temperature raised ballistically, and its contents flushed into the GC/MS or similar device for chemical analysis in step 518.

In order to ensure that chemicals collected in one sample do not affect the accuracy or precision of further sampling events, the collection line must be completely cleared. While the fused silica coating of the collection line helps to ensure that the collected chemicals do not bind to its inner wall, the collection line is preferably raised to greater than 200°, preferably about 300°, and back-flushed to ensure that any condensate or adsorbed chemicals in the line are removed in step 520.

Figure 6:
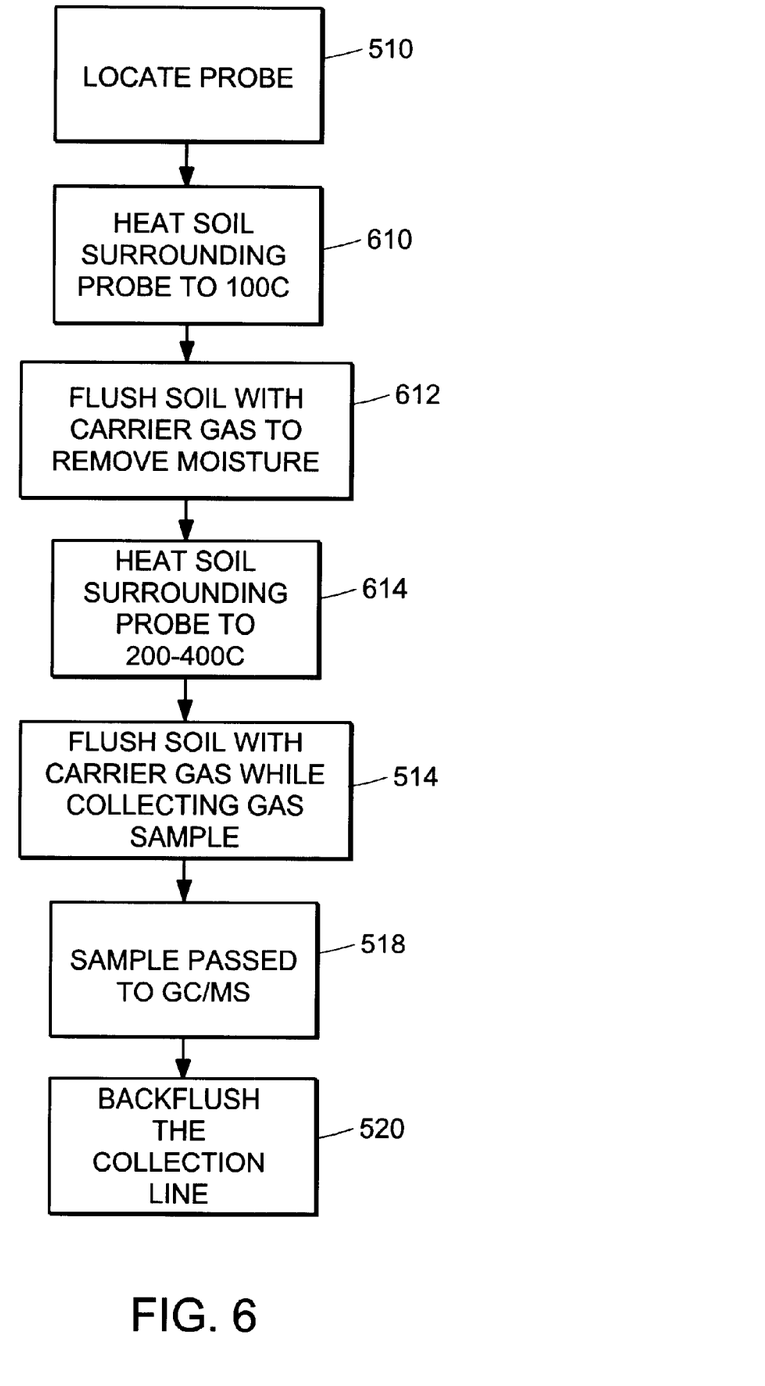
FIG. 6 is another process diagram illustrating the use of inventive penetrometer system in soils with a high moisture content.

FIG. 6 is a process diagram illustrating chemical sampling in geologic media having a high moisture content. High amounts of water contained in the soil reduce the efficiency with which the chemicals can be drawn from the soil and also tend to dilute any chemicals collected in the adsorber unit 430. In this method, the probe 200 is first placed at the desired depth in step 510 as in the previously-described method. The temperature of the probe 200 is raised to only 100–120° C. in step 610. Carrier gas is then flushed into the surrounding soil preferably through both the collection port 218 and the carrier gas port 216 in step 612. The heating of the surrounding soil by the probe 200 and the carrier gas flushing has the effect of pushing the moisture away from the collection port 218. Research suggests that, the moisture needs only to be pushed approximately 3–4 millimeters away from the port to avoid excess water in the sample.

Once moisture flushing of the soil has been accomplished, the temperature of the probe is raised to a temperature that will debind any chemicals of interest from the soil. In the preferred embodiment, the temperature of the probe is raised 200°, but preferably as high as 400° C. in step 614. At this point, collection occurs as described previously in FIG. 5 in step 514, with the sample being passed to the GC/MS in step 518. Back flushing is then performed in step 520.

Figure 7:
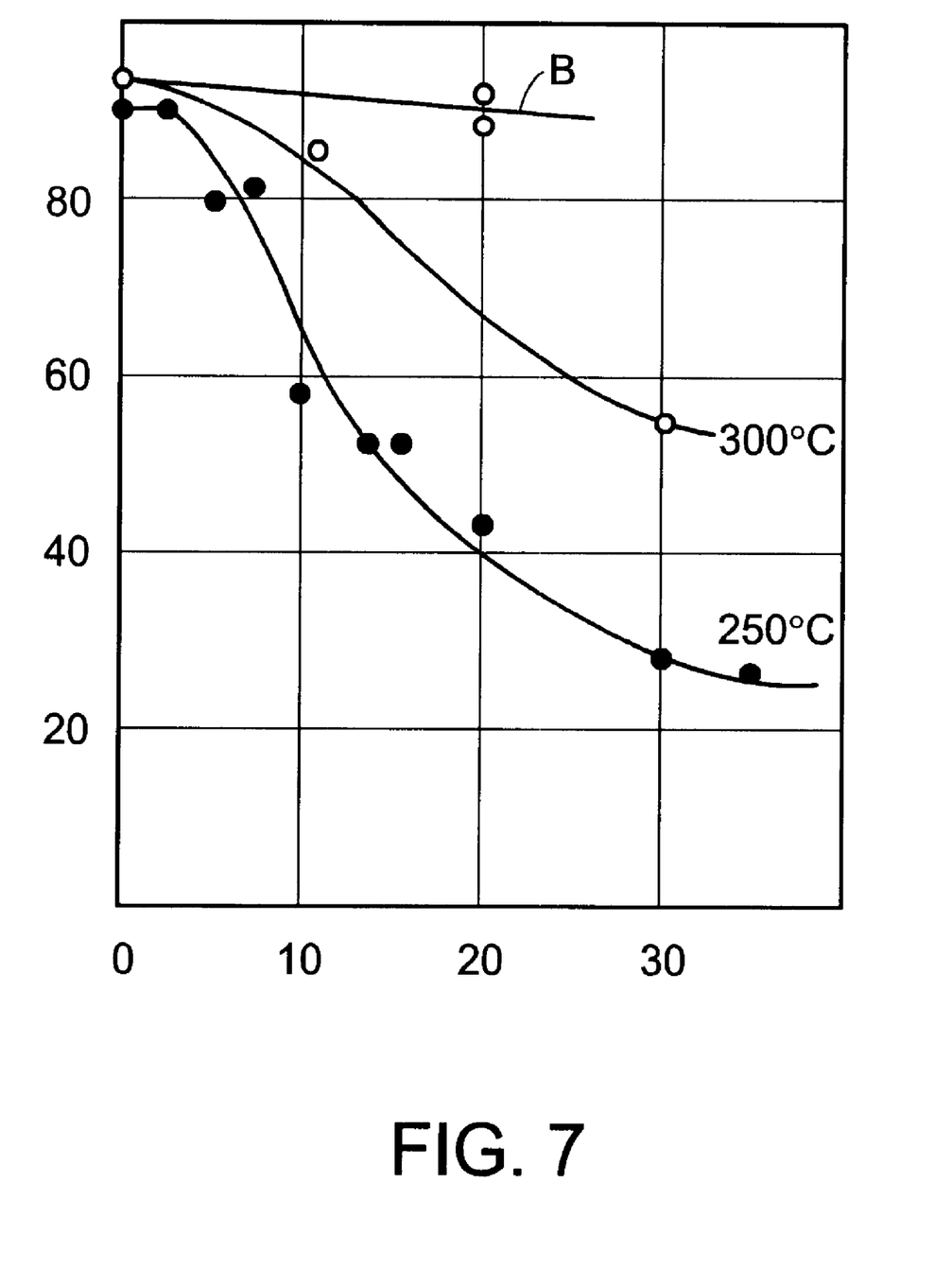
FIG. 7 is a plot of percent PCB recovery as a function of percent soil moisture content for various temperatures and when the process of FIG. 6 is used.

FIG. 7 is a plot of PCB recovery as a function of soil moisture, illustrating the enhanced collection that can be achieved using the moisture flushing process of FIG. 6. PCB recovery drops markedly with soil moisture even when high probe temperatures of 250 and 300° C. soil are applied. Line B is data collected when moisture flushing is first performed. Statically the same results are obtained between 0 and 20% soil moisture content when flushing is first performed.

FURTHER EXPERIMENTAL DATA

Figure 8:
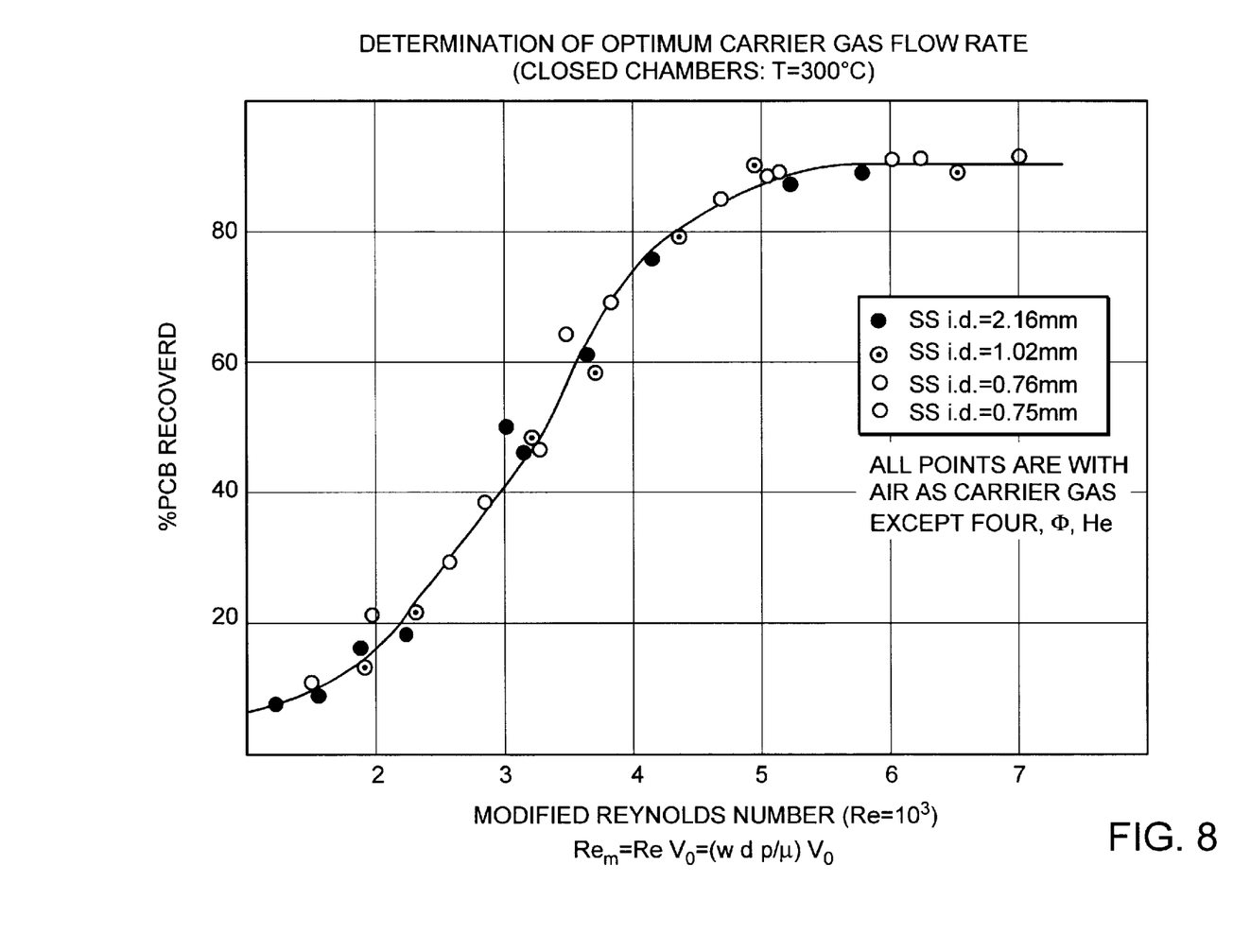
FIG. 8 is a plot of percent PCB recovery as a function of the modified Reynolds number showing the optimum carrier gas flow rate, temperature, and collection volume.

FIG. 8 is a plot of percent PCB recovery as a function of the modified Reynolds Number ($Re_m = ReV_o = (wd\rho/\mu)V_o$).

This graph assists in the determination of the optimum carrier gas flow rate, temperature and collected volume. As suggested by the graph, recovery peaks at approximately a modified Reynolds Number of 5000. The various inside diameters (i.d.) of the lines tested, SS i.d.=2.16 mm, 1.02 mm, 0.76 mm, and 0.75 mm, and lengths of 20–40 ft., suggest that performance is not dependent on i.d., length or inert carrier gas used.

A closed cell experimental set up was used to determine to optimum extraction temperatures and carrier gas flow rates for organics collection from soil. In order to test the efficiency with which the inventive probe can collect bound chemicals from a soil sample, the performance of the probe was compared against vapor collection from a closed chamber. Closed cell conditions represent the maximum amount that can be extracted since none of the vapor produced is lost to the environment and all soil is uniformly heated.

Table I is a comparison of the probe's collection efficiency compared against the closed chamber. For the test, the temperature of the transfer line was 280° C., soil temperature was 280° C., $Re_m$ was 6,000, $w_g$=1.2 m/s; and L/d=15.

sented by the organic recovery percent standard deviation (%RSD) is as good as solvent extraction experiments. Material balance calculations indicate that about 2% of the PAH organic was adsorbed onto the transfer line with the remaining organic left in the soil. Note that five minutes of back flushing the collection line resulted in non-detectable levels left within the line. Approximately 65% recovery was found for the inventive probe as compared to the 90% recovery in the closed cell for PCBs.

To determine the probe's performance with respect to complex sample matrixes, PAH contaminated soil samples were collected from a coal-fired utility plant located in Lynn, Mass. Table II depicts the PAH collection efficiency by solvent extraction, closed chamber, and inventive probe. The percent recoveries between the closed chamber and the probe measurements were statistically the same for this sample as was found for the fortified sample (Table I). When compared to solvent extraction (the so-called "true" measured concentration), the thermally extracted results were

TABLE I

PROBE'S PERCENT RECOVERY

|  | 50-PPM | 25-PPM | 15-PPM | 5-PPM | AVE REC | % RSD | CLOSED CHAMBER % REC | % DIFF |
|---|---|---|---|---|---|---|---|---|
| Naphthalene | 20 | 37 | 26 | 37 | 30 | 23 | 18 | 68 |
| Acenaphthylene | 34 | 36 | 36 | 33 | 35 | 5 | 62 | 44 |
| Acenaphthene | 41 | 39 | 33 | 30 | 36 | 18 | 77 | 53 |
| Fluorene | 49 | 36 | 38 | 37 | 40 | 17 | 73 | 46 |
| Phenanthrene | 37 | 32 | 35 | 34 | 35 | 7 | 80 | 57 |
| Anthracene | 37 | 32 | 34 | 34 | 34 | 7 | 77 | 56 |
| Fluoranthene | 65 | 53 | 48 | 36 | 50 | 34 | 80 | 37 |
| Pyrene | 64 | 53 | 45 | 68 | 57 | 15 | 85 | 32 |
| Chrysene | 27 | 37 | 31 | 41 | 34 | 16 | 57 | 40 |
| Benzo (a) anthracene | 49 | 37 | 36 | 41 | 40 | 12 | 62 | 36 |
| Benzo (b&k) fluoranthene | 29 | 27 | 29 | 23 | 27 | 12 | 48 | 44 |
| Benzo (a) pyrene | 25 | 23 | 36 | 24 | 27 | 26 | 65 | 58 |
| Indeno (1,2,3-ed) pyrene | 26 | 19 | 20 | 23 | 22 | 14 | 65 | 31 |
| Dibenz (a,b) anthracene | 26 | 19 | 19 | 23 | 22 | 14 | 62 | 32 |
| Benzo (g,h,i) perylene | 17 | 16 | 16 | 16 | 16 | 4 | 20 | 19 |

The accuracy of the probe approximates one-half that of the closed, ideal system. Measurement precision as represented by the organic recovery percent standard deviation less. Solvent extraction, however, can not be used for in situ testing.

TABLE II

|  | Solvent Extraction, ppm | Closed ppm | % Rec | Probe ppm | % Rec | % Diff |
|---|---|---|---|---|---|---|
| Naphthalene | 1267 | 431 | 34 | 405 | 32 | 6 |
| Acenaphthylene | 351 | 200 | 57 | 112 | 32 | 44 |
| Acenaphthene | 297 | 196 | 66 | 110 | 37 | 44 |
| Fluorene | 441 | 273 | 62 | 154 | 35 | 44 |
| Phenanthrene | 865 | 562 | 65 | 355 | 41 | 37 |
| Anthracene | 866 | 563 | 65 | 355 | 41 | 37 |
| Fluoranthene | 567 | 437 | 77 | 227 | 40 | 48 |
| Pyrene | 1070 | 760 | 71 | 439 | 41 | 42 |
| Benzo (a) anthracene | 536 | 322 | 60 | 166 | 31 | 48 |
| Chrysene | 535 | 321 | 60 | 166 | 31 | 48 |
| Benzo (b) fluoranthene | 284 | 114 | 40 | 62 | 22 | 45 |
| Benzo (k) fluoranthene | 284 | 114 | 40 | 62 | 22 | 45 |
| Benzo (a) pyrene | 427 | 209 | 49 | 141 | 33 | 33 |
| Dibenz (a,h) anthracene | 186 | 48 | 26 | 32 | 17 | 35 |
| Indeno (1,2,3-cd) pyrene | 187 | 49 | 26 | 32 | 17 | 35 |
| Benzo (g,h,i) perylene | 132 | 25 | 19 | 15 | 11 | 42 |

While this invention has been particularly shown and described with references to preferred embodiments thereof, it will be understood by those skilled in the art that various changes in form and detail may be made therein without departing from the spirit and scope of the invention as defined by the appended claims.

What is claimed is:

1. A thermal extraction probe system for subsurface chemical detection, the probe system comprising:
   a probe;
   rigid pipe sections for transmitting force to advance the probe;
   a heater that controls a temperature of a geologic medium surrounding the probe;
   at least one carrier gas port located on the probe that exhausts a carrier gas into the geologic medium;
   at least one collection port on the probe that collects fluids from the geologic medium for analysis;
   a collection tube extending from the collection port to a surface for conveying a collected fluid sample from the collection port to the surface, the collection tube being flexible to enable passage through the pipe sections when disconnected for storage; and
   a collection unit at the surface for receiving the fluid sample from the collection tube.

2. The probe system described in claim 1, further comprising at least two collection ports and at least two carrier gas ports spaced around a circumference of the probe.

3. The probe system described in claim 1, further comprising at least two collection ports and at least two carrier gas ports spaced axially along the probe.

4. The probe system described in claim 1, further comprising temperature transducer that detects the temperature of the geologic medium surrounding the probe.

5. The probe system described in claim 1, wherein the heater raises the temperature of the geologic medium to greater than 200° C.

6. The probe system described in claim 1, wherein the heater raises the temperature of the geologic medium to approximately 400° C. or greater.

7. The probe system described in claim 1, further comprising:
   a pipe section that serves as an outer probe housing and through which the carrier gas port and collection port extend;
   a cartridge, containing the heater, that is inserted into the pipe section.

8. The probe system described in claim 1, further comprising a heated transfer line system, comprising:
   the collection line;
   a flexible carrier gas line that conveys a carrier gas to the carrier gas port to facilitate the collection of the fluid sample; and
   means for heating the collection line.

9. The probe system described in claim 8, further comprising at least one thermally insulating layer surrounding the collection line.

10. The probe system described in claim 8, wherein the collection line heating means comprises a heat source laid in proximity to the collection line at least partially along a length of the transfer line system.

11. The probe system described in claim 8, wherein the collection line heating means evenly heats the collection line along an entire length of the transfer line system.

12. The probe system described in claim 8, wherein the collection line heating means is capable of raising a temperature of the collection line to at least 100° C.

13. The probe system described in claim 8, wherein the collection line heating means is capable of raising a temperature of the collection line to approximately 200° C.

14. The probe system described in claim 8, further comprising a temperature transducer that detects a temperature of the collection line at least at one point along a length of the transfer line system.

15. The probe system described in claim 8, further comprising at least one slippery layer and insulation layers surrounding at least the collection line, the slippery layer facilitating movement between layers in the heated transfer line system.

16. The probe system described in claim 8, wherein the collection line and the carrier gas line convey the fluid sample and the carrier gas between a chemical analyzer and the remote probe.

17. The probe system described in claim 16, further comprising electrical cables that facilitate control of the remote probe.

18. The probe system described in claim 8, wherein the line is at least 50 feet long.

19. The probe system described in claim 8, wherein the collection line is inert with respect to the fluid sample and does not catalyze any reactions in the fluid sample it transports.

20. The probe system described in claim 8, wherein the transfer line system has a bending radius of approximately ten inches or less.

21. The probe system described in claim 8, wherein the transfer line system has a bending radius of approximately four inches or less.

22. A method for thermally extracting subsurface chemicals in soil with a high water content, the method comprising:
   advancing a probe through the soil to a desired sampling depth;
   heating the soil surrounding the probe at the sampling depth to at least 100° C.;
   exhausting a carrier gas into the soil at the sampling depth, which has been heated to the at least 100° C., to push the water away from a collection port;
   heating the soil to substantially higher than 100° C.; and
   collecting fluids from the soil in a collection line through the collection port at the sampling depth.

23. The method described in claim 22, wherein the step of heating the soil to substantially higher than 100° C. comprises heating the soil surrounding the probe to greater than 400° C.

24. The method described in claim 22, further comprising backflushing any remaining vapor from the collection line.

25. A method described in claim 22, further comprising:
   conveying the fluid sample through the collection line to the surface;
   controlling a temperature of the collection line to facilitate the movement of the sample through the line; and
   receiving the chemical sample at a sample collection unit.

26. The method described in claim 25, wherein the collection unit also analyzes the chemical sample.

27. The method described in claim 25, further comprising mixing a carrier gas with the fluid sample to facilitate its movement into and through the collection line.

28. The method described in claim 25, further comprising heating the fluid sample prior to its being drawn into the sampling port.

29. The method described in claim 25, further comprising:
   maintaining or increasing a temperature of the collection line; and flushing the collection line after sampling to purge the collection line for the next chemical sample.

30. A thermal extraction probe for subsurface chemical detection, the probe comprising:

a heater that controls a temperature of a geologic medium surrounding the probe;

at least one carrier gas port located on an side wall of the probe that exhausts a carrier gas into the geologic medium;

at least one collection port also on the external side wall of the probe that collects fluids from the geologic medium for analysis;

a pipe section that serves as an outer probe housing;

a cartridge, containing the heater, that is inserted into the pipe section;

at least one carrier gas line and at least one collection line in communication with an exterior of the pipe section; and at least one plug that is radially inserted in a hole in the pipe section, the carrier gas port and the fluid collection port being formed in the plug and being in fluid communication with the carrier gas line and the collection line, respectively.

31. A thermal extraction probe for subsurface chemical detection, the probe comprising:

a heater that controls a temperature of a geologic medium surrounding the probe;

at least one carrier gas port located on an side wall of the probe that exhausts a carrier gas into the geologic medium;

at least one vapor collection port also on the external side wall of the probe that collects vapors from the geologic medium for analysis;

a flexible, electrically-conductive collection line that conveys a collected fluid sample from the vapor collection port;

a flexible carrier gas line that conveys a carrier gas to the carrier gas port to facilitate the collection of the fluid sample; and an electrical power source that generates a current through the collection line so that a resistance of the collection line generates heat.

32. The probe described in claim 31, further comprising at least one electrically insulating layer surrounding the collection line.

* * * * *